United States Patent [19]

Barone

[11] 3,974,228

[45] Aug. 10, 1976

[54] PREPARATION OF HYDROPEROXIDES BY AUTOXIDATION

[75] Inventor: Bruno J. Barone, Houston, Tex.

[73] Assignee: Petro-Tex Chemical Corporation, Houston, Tex.

[22] Filed: Mar. 10, 1975

[21] Appl. No.: 556,885

Related U.S. Application Data

[63] Continuation-in-part of Ser. No. 29,679, April 17, 1970, abandoned.

[52] U.S. Cl. .................. 260/610 B; 260/593 R; 260/632 C
[51] Int. Cl.$^2$.................................. C07C 179/02
[58] Field of Search ............ 260/610 B; 29/679

[56] References Cited
UNITED STATES PATENTS

| | | | |
|---|---|---|---|
| 2,447,794 | 8/1948 | Brewer | 260/610 B |
| 2,510,526 | 5/1970 | Bonnert et al. | 260/610 B |
| 2,632,774 | 3/1953 | Conner et al. | 260/610 B |
| 2,773,906 | 12/1956 | Emerson | 260/610 B |
| 2,776,994 | 1/1957 | Joris | 260/610 B |
| 2,798,096 | 9/1957 | Baumgartner | 260/610 B |

FOREIGN PATENTS OR APPLICATIONS

| | | | |
|---|---|---|---|
| 716,106 | 4/1965 | Canada | 260/610 B |
| 44-9891 | 9/1969 | Japan | 260/610 B |
| 700,546 | 12/1953 | United Kingdom | 260/610 B |

*Primary Examiner*—James O. Thomas, Jr.
*Assistant Examiner*—W. B. Lone
*Attorney, Agent, or Firm*—N. Elton Dry; Kenneth H. Johnson

[57] ABSTRACT

In autoxidation of tertiary cycloalkanes and alkyl aromatics the selectivity for organic hydroperoxides can be substantially increased by using a basic or amphoteric buffering compound of a Group IIIB or rare earth metal. For example, an autoxidation of isopentane with 4 wt. percent LaO at 11.1 mole percent conversion gave selectivities of t-amyl hydroperoxides — 75.5 mole percent, acetone — 18.3 mole percent, and t-amyl alcohol — 0.3 mole percent. The same reaction without the buffer at only 10.3 mole percent conversion ve selectivities of t-amyl hydroperoxide — 30.6 mole percent, acetone — 51.2 mole percent and t-amyl alcohol — 14.9 percent.

10 Claims, No Drawings

PREPARATION OF HYDROPEROXIDES BY AUTOXIDATION

This application is a continuation-in-part of Ser. No. 29,679 filed Apr. 17, 1970, and now abandoned.

BACKGROUND OF THE INVENTION

The present invention relates to the preparation of the hydroperoxides of tertiary alkanes, cycloalkanes and alkyl aromatics. More particularly it relates to the autoxidation of tertiary alkanes and cycloalkanes in the presence of a buffering material. The term autoxidation is understood to mean the reaction of a substance with molecular oxygen without the intervention of a flame. The hydroperoxides of tertiary alkanes, and cycloalkanes have been prepared by autoxidation. Generally, the results of these preparations have been rather discouraging. Two somewhat out dated but comprehensive reviews of the prior art of peroxides are "Organic Peroxides, their formation and reactions", E. G. E. Hawkins, D. Van Nostrand Company, Inc., Princeton, N.J. 1961, and "Organic Peroxides", A. G. Davies, Butterworths, London, 1961, which are incorporated herein insofar as they describe the prior art.

Most known autoxidation reactions for the tertiary cycloalkanes and alkyl aromatics have relatively low selectivities for the hydroperoxides. Generally, the product of such oxidations has been a mixture of oxidation products, e.g., the aldehydes, ketones, alcohols, acids, hydroperoxides, water and carbon dioxide. If the desired product is a hydroperoxide then the production of such by-products and the necessity of removing some or all of them from the hydroperoxide makes an economically unattractive process. A preferable process would be one that had high selectivity for the hydroperoxide with few and relatively low concentrations of by-products. Such a process would be attractive even if low conversions were necessitated, since the hydrocarbon starting material makes an excellent diluent for the potentially dangerous hydroperoxide. Very often a product such as that described above can be used directly or with a minimum of treatment for the purification and concentration of the hydroperoxide.

It is an object of this invention to provide an improved process for the autoxidation of tertiary alkanes, cycloalkanes and alkyl aromatics to produce hydroperoxides. It is a further object to provide a process which has high selectivity for hydroperoxides. These and other objects will become apparent from the discussion below.

SUMMARY OF THE INVENTION

It has been found that organic hydroperoxides can be obtained by a process comprising contacting a tertiary alkane, cycloalkane or alkyl aromatic with molecular oxygen in liquid phase in the presence of a buffer comprising a basic or amphoteric compound of a metal selected from Groups IIIB, the rare earths of the Period Table of Elements or mixtures thereof.

The metals employed are those of Groups IIIB and the rare earths, e.g., Sc, Y, La, Ac, Ce, Pr, Nd, Pm, Sm, Eu, Gd, Tb, Dy, Ho, Er, Tm, Yb, Lu, Th, Pa or U. A preferred group consists of La, Gd, Pr, Nb, and Th, with the most preferred metals for this purpose being La and Gd. The metal compounds employed are either basic or capable of acting basic, i.e., amphoteric and include for the most part the carbonates, oxides, hydroxides and bicarbonates (where they exist). Some specific compounds that exhibit this property of basicity are $Pr_2O_3$, $Nd_2O_3$, $ThO_2$,. The acidic compounds of various metals, are totally unsuited.

Various mixtures of metal buffers can be used. For example, the oxides of various metals can be used or various basic and amphoteric compounds of a single metal or mixture of metals can be used.

It is theorized, without intending any limitation to the scope of the present invention that the function of the basic of amphoteric metal compound is at least twofold in the reaction. First, the metal compound serves to absorb any metal ions in the reaction medium thus reducing the possibility of further oxidation, which may be catalyzed by such stray ions and secondly, in a similar manner the buffer absorbs acids that are formed, reducing the possibility of side reaction acid catalysis. The buffer compound also scavages water than is produced in the system, maintaining an essentially anhydrous system, although this may not be as important a function in the system.

Generally, the buffer will be employed in an amount sufficient to passivate the reaction system, i.e., a passivating amount. The buffer compound can be of some value in concentrations as low as 0.05 weight percent, although it would be more useful and preferable at 0.2 weight percent based on the hydrocarbon feed. The upper limit of buffer that can be employed is determined by economic consideration and the feasibility of recovering the product. Generally, no more than 25 weight percent of the buffer would be employed and preferably 10 or less weight percent. It has been observed that there is a decrease in the selectivity of the reaction for hydroperoxides as the conversion is increased in the presence of a given amount of buffer. The effect on hydroperoxide selectivity can be somewhat mitigated by the use of additional quantities of buffer. Within the specified ranges one skilled in the art will be able to select the quantity of buffer for a desired product distribution at a desired economic cost and ease of operation.

The process of the present invention is used for the preparation of hydroperoxides from tertiary alkanes, cycloalkanes and alkyl aromatics. Suitably, the tertiary alkanes, cycloalkanes and alkyl aromatics would have from 3 to 30 carbon atoms, preferably 4 to 10 and most preferably 5 to 8 carbon atoms. The carbons of the tertiary carbon atom may be primary, secondary or tertiary, thus there may be more than one tertiary carbon atom in a compound. Some examples of tertiary alkanes intended to be included are isobutane, isopentane, 2-methyl pentane, 3-methyl hexane, 2,3-dimethyl hexane, 4-methyl heptane, 4-n-propyl heptane, 3-tertiary butyl-hexane, 2-methyl decane, 2,6-dimethyl-3-isopropyl heptane, 2,11-dimethyl dodecane, 2-methylheptadecane, 7-isopropylhexadecane, 4-n-propyl-nonadecane, 10-n-nonyl-n-nonadecane and the like. The cycloalkane may be mono, di or tri cyclo, etc. unsubstituted or substituted with hydrocarbons. The hydrocarbon substituent will usually contain 1 to 10 carbon atoms and may be branched or unbranched. Suitable cycloalkanes include for example cyclopropane, propylcyclopropane, 1-methyl-2 (2-methyl propyl) cyclopropyl, cyclobutane, 1,2-dimethyl-cyclobutane, 1,2-diisopropylcyclobutane, cyclopentane, ethyl cyclopentane, cyclohexane, 1,2,4-trimethyl cyclohexane, propylcycloheptane, cyclooctane, methylcyclooctane, cycloundecane, cyclododecane, cyclooctadecane, cyclotriacontane, cyclopentylcyclopentane, cyclopentylcyclohexylmethane, bicyclohexane, [0,3,3] bicyclooctane, perhydrophenanthrene, 1,3-dimethyl 7-isopropyl-2,3-(3-methyl-cyclohexano) -[0,4,4] -bicyclodecane and the like. Suitable alkyl aromatics, for example, include ethyl benzene, propyl benzene, isopropylbenzene, cumene, p-cymene, p-diisopropylbenzene, p-ethyl-isopropyl-benzene, and the like. A particularly preferred group of hydrocarbons for use in the present process are isobutane, isopentane, isohexane, isoheptane, isooctane, cyclopentane, cyclohexane cycloheptane, ethyl benzene and cumene.

As stated above the tertiary alkane may contain secondary and other tertiary groups, likewise the cycloalkane can contain various hydrocarbon sutstituents as well as more than one cyclic structure. The aryl and alkaryl groups need not be derived from benzene as is the case in p-cymene, for example, since compounds containing aromatic nuclei, such as those derived from naphthalene, anthracene and phenanthrene, also are operable. The latter compounds, however, being solids, must be dissolved in a suitable solvent such as benzene during the oxidation. The aryl group may be substituted with alkyl groups, as illustrated by the methyl group in p-cymene and the isopropyl group in p-diisopropylbenzene, and the groups may, for example, be methyl, ethyl, propyl, isopropyl, butyl, isobutyl, secondary butyl, tertiary butyl, and the like. Such highly branched and substituted hydrocarbons are generally suitable for the present process, however, it should be borne in mind that presence of more than one tertiary group on the tertiary alkane or the presence of alkyl substituents, particularly tertiary substituents on the cycloalkane, can result in a great profusion of products since the number of principal active sites is increased with each substitution. That is not to say that all of the sites even of the same or similar grouping will possess the same degree of activity. Other factors such as the electron density, steric and kinetic considerations, and the like, may for the most part control such activity. In any event, it should be expected that use of exotic or complex hydrocarbon starting materials will probably give lower selectivities to the desired hydroperoxides. In the present examples such complicating reactions are largely avoided by the use of a relatively simple tertiary alkane, i.e., isopentane, which will demonstrate the type of reaction and the advantages that can arise from the present process.

Tertiary alkanes and cycloalkanes as described herein above form a preferred group of hydrocarbon reactants for the present invention.

The reactions of the present process result in hydroperoxides corresponding to the starting hydrocarbon. Since the tertiary carbon is the most reactive in the autoxidation, the product is almost entirely the tertiary hydroperoxide. The secondary carbon atoms in unsubstituted cycloalkanes and alkyl aromatics are similar to the tertiary groups and react accordingly; however, a tertiary carbon is the preferred reaction site in the substituted cycloalkanes or alkyl aromatics. The following examples will demonstrate the reaction: Isobutane to tertiary-butyl hydroperoxide, isopentane to tertiary-amyl hydroperoxide, isohexane to tertiary-hexyl hydroperoxide, cyclopentane to cyclopentyl hydoperoxide, decalin to decalin-4'-hydroperoxide.

The present invention reaction is an autoxidation carried out at somewhat elevated temperatures. Generally the temperatures which are most suitable for the oxidation will be between 110°–160°C. and more preferably about 130°–150°C. In autoxidations there is usually an induction period during which the reaction proceeds very slowly. During this period the production of hydroperoxide is slow, however, when a sufficient concentration of hydroperoxide is achieved the reaction is initiated as its "real" reaction rate. The induction period can be reduced by the use of high initial temperatures, i.e., 160°–170°C. which will allow the rapid build up of hydroperoxide. However, once the reaction is initiated the temperature is reduced, e.g., 130°–150°C. Temperatures higher than 160°C should not be employed after the reaction has been initiated since the possibility of further oxidation of the peroxide is enhanced.

The induction period mentioned above can also be reduced by the addition of an initiator such as some of the hydroperoxide product to be produced. Other initiators are free radical initiators such as α-methyl benzyl hydroperoxide, α-methyl-p-methylbenzenyl hydroperoxide, α-methyl-α'-n-propyl-p-xylylene dihydroperoxide, ethyl acetoacetate, phenylacetone, acetylacetone and the like.

The autoxidation is carried out by contacting the tertiary alkane in liquid phase at the temperatures and conditions set out herein with molecular oxygen. The oxygen can be furnished as pure oxygen or in gases containing oxygen, e.g., air or mixtures of oxygen with inert gases, such as helium or nitrogen in the same or substantially different proportions as oxygen is found in air.

Sufficient pressure is employed so as to maintain the reaction mixture in liquid phase. This will usually require more than atmospheric pressure, although some of the hydrocarbons encompassed herein are liquid at atmospheric pressure at temperatures up to 170°C. Generally, however, pressure will be required. It is not necessary to use any more pressure than is necessary to maintain the liquid phase since oxygen is not believed to be the rate determining factor in the reaction. Pressures of atmospheric up to about 1000 psi will usually be sufficient.

Diluents can be used, for example, benzene, toluene, xylene, naphthalene, tert-butyl alcohol, tert-amyl alcohol, nitrobenzene, carbon tetrachloride, and the like. It should be noted that such diluent will decrease the rate of reaction. Generally, the unreacted feed material will be a sufficient diluent for this reaction. The usual metal oxidation catalyst should not be present during the present reaction and any solvent should be examined to be sure it is free of such contaminants.

In carrying out the process it has been found that the best results are obtained when the buffer compound is thoroughly dispensed in the reaction medium. This is best achieved by agitation of the reaction medium for example, by high speed stirring. An aid to maintaining the dispersion would be the use of very fine powders such as below about 20 micron size. The buffer compound is easily recovered since it is a solid in the reaction system. The buffer can be regenerated or converted to the oxide by calcining.

The following examples will illustrate the operation of the invention and the advantages to be derived therefrom. The apparatus used in each of the following examples was 3,000 psi magnetically stirred, 1.4 liter, stainless steel autoclave, equipped with a Dispersamax agitator, reflux condenser and internal water cooling coil. The isopentane feed, and other materials for the reaction were charged to the reactor. Oxygen containing gas was added continuously with sufficient pressure to maintain the liquid phase. Inlet gas was measured by following the pressure drop in a standardized metering vessel and fed into the autoclave through a ballast type pressure regulator. Exit gas, at atmospheric pressure, was then passed through three dry ice traps, an ascarite trap, a wet test meter and then vented. Pure oxygen was employed in the present examples unless otherwise indicated. When an oxygen containing gas other than pure oxygen was employed, a Beckman E-2 oxygen anaylzer was inserted after the dry ice traps and the oxygen constant of the off gases monitored so that the reaction was not oxygen starved. This can be avoided by adjusting the gas flow to provide a minimum oxygen content for the off gases, e.g., more than about 3 vol. percent. Analysis was by gas chromatograph and idometric titration for hydroperoxides.

EXAMPLE 1

The examples demonstrate the process run with a buffer. The pressure was 600 oxygen at 140°C. The other conditions and the results are in Table I.

TABLE I

| Example No. | 1 |
|---|---|
| Reactants | |
| Isopentane | 600 |
| Reaction Conditions | |
| Total Reaction Time, hrs. | 2.25 |
| Results | |
| Induction Period, min. | 94.5 |
| Oxygen Consumed, mole | 1.103 |
| Carbon Dioxide Produced, mole | 0.042 |
| Hydroperoxide Concentration, percent | 4.40 |
| Isopentane Consumed, percent | 10.3 |
| Percent Selectivity (Mole Product/100 Mole of Hydrocarbon Consumed) | |
| Acetone | 51.2 |
| t-Amyl Alcohol | 14.9 |
| t-Amyl Hydroperoxide | 30.6 |

EXAMPLES 2 – 6

This set of examples shows the use of a number of oxides of compounds from Groups IIIB and rare earths of the Periodic Table. The pressure was 500 psi oxygen and the other conditions and results are in Table II.

TABLE II

| Example No. | 2 | 3 | 4 | 5 | 6 |
|---|---|---|---|---|---|
| Reactants | | | | | |
| Isopentane, g. | 600 | 100 | 100 | 100 | 100 |
| Lanthanum Oxide, g | 25 | — | — | — | — |
| Gadolinium Oxide, g | — | 4.0 | — | — | — |
| Praseodymium Oxide, g | — | — | 4.0 | — | — |
| Neodymium Oxide, g | — | — | — | 4.0 | — |
| Thorium Oxide, g | — | — | — | — | 4.0 |
| Reaction Conditions | | | | | |
| Temperature, °C. | 140 | 140 | 140 | 140 | 130 |
| Total Reaction Time, hrs. | 4.33 | 3.67 | 3.33 | 3.0 | 4.17 |
| Results | | | | | |
| Induction Period, Min. | 88 | 90 | 58 | 70 | 102 |
| Oxygen Consumed, mole | 0.835 | 0.091 | 0.147 | 0.139 | 0.153 |
| Carbon Dioxide Produced, mole | 0.002 | 0.0002 | 0.006 | 0.001 | 0.005 |
| Hydroperoxide Content, percent | 11.93 | 7.29 | 7.29 | 8.42 | 6.88 |
| Isopentane Consumed, percent | 11.1 | 6.8 | 10.8 | 11.0 | 8.1 |
| Percent Selectivity (Mole Product/100 Mole Hydrocarbon Cumsumed) | | | | | |
| Acetone | 18.3 | 15.1 | 28.0 | 30.5 | 35.0 |
| t-Amyl Alcohol | 0.3 | 6.5 | 18.5 | 11.7 | 3.0 |
| t-Amyl Hydroperoxide | 75.5 | 70.1 | 47.2 | 53.1 | 59.0 |

Generally it would be most preferably to have the highest selectivities to hydroperoxides possible, however, the very nature of the desired product, the hydroperoxide, makes this a difficult task. The present process does provide for startlingly high hydroperoxide selectivities at reasonable conversion rates. In fact, the buffer compounds of the present invention provide relatively high selectivities at increasing conversion rates. The loss in selectivity for hydroperoxides is picked up by other products, e.g., predominately the ketone and alcohol (other possible by-products include aldehydes, acids, $CO_2$, CO and $H_2O$). The buffers of the invention tend to suppress rapid increases for ketone and tend to favor the alcohol selectivity which is an unexpected benefit from the point of view of the by-products. Ketones can be valuable by-products but are more commonly problems. The ketone is, of course, the result of the degradative oxidation of the hydroperoxide. Thus, there is a scission in the carbon chain, meaning that for every mole of ketone there is a mole of yet another by-product. The alcohol on the other hand is an excellent diluent for the hydroperoxide. Compositions comprising principally hydroperoxides and alcohol (in a hydrocarbon diluent, i.e., the starting material) can be used directly in other processes. For example, a process discribed in U.S. Pat. No. 3,351,635 uses a solution of a hydroperoxide (prepared in liquid phase by autoxidation) in a hydrocarbon, along with some of the alcohol formed during the oxidation, to form oxirane compounds by reacting with an olefinically unsaturated compound. The highly reactive ketones are a detriment to a process such as that disclosed in U.S. Pat. No. 3,351,635 and other similar reactions where the alcohol can be tolerated.

The alcohols as such are quite valuable since they are easily dehydrated by conventional means to the corresponding olefins.

In addition to serving as reactants the organic hydroperoxides are excellent free radical initiators and their use for this purpose being well known and widespread.

The hydroperoxides can be concentrated by conventional means such as neat crystallization, distillation or extraction. Those familiar with hydroperoxides are aware of their tendency on occasion to undergo violent decomposition and the usual safety measures should be taken for personnel and equipment.

The invention claimed is:

1. In the process of preparing organic hydroperoxides comprising contacting a hydrocarbon of a tertiary alkane, cycloalkane or alkyl aromatic compound, said hydrocarbon having 3 to 30 carbon atoms, with molecular oxygen at a temperature in the range of about 110°–170°C and a pressure sufficient to maintain the reactants in liquid phase, wherein the improvement is in conducting said process in the presence of at least 0.05 weight percent of a buffer comprising a carbonate, oxide or hydroxide of a metal selected from the group consisting of La, Gd, Pr, Nb, and Th,.

2. The process according to claim 1 wherein the temperature in the range of 130° to 150°C.

3. The process according to claim 1 wherein the pressure is from atmospheric up to about 1000 psi.

4. The process according to claim 1 wherein there is about 0.05 to 25 weight percent of the buffer present.

5. The process according to claim 4 wherein the hydrocarbon is a tertiary alkane or cycloalkane.

6. The process according to claim 5 wherein said hydrocarbon is selected from the group consisting of isobutane, isopentane, isohexane, isoheptane, isooctane, cyclopentane, cyclohexane and cycloheptane.

7. The process according to claim 6 wherein the buffer is $La_2O_3$.

8. The process according to claim 6 wherein the buffer is $Gd_2O_3$.

9. The process according to claim 1 wherein the buffer is $La_2O_3$, $Gd_2O_3$, $Pr_2O_3$, $Nb_2O_3$, or $THO_2$.

10. The process according to claim 1 wherein the hydrocarbon is isobutane and the hydroperoxide is tertiary butyl hydroperoxide.

* * * * *

UNITED STATES PATENT OFFICE
CERTIFICATE OF CORRECTION

PATENT NO. : 3,974,228
DATED : August 10, 1976
INVENTOR(S) : Bruno J. Barone

It is certified that error appears in the above-identified patent and that said Letters Patent are hereby corrected as shown below:

IN THE ABSTRACT, line 11 reads "ve selectivities" but should read --gave selectivities--.
Col. 1, line 59, reads "Period Table" but should read--Periodic Table--.
Col. 1, line 64, reads "Nb" but should read--Nd--.
Col. 3, line 15, reads "sutstituents" but should read--substituents--.
Col. 3, line 66 reads "The present invention reaction" but should read --The present reaction--.
Col. 4, line 1 reads "be between 110 - 160°C" but should read--be between about 110 - 160°C--.
Col. 4, line 7 reads "as its 'real' " but should read--at its "real"--.
Col. 4, line 65 reads "was 3,000 psi" but should read--was a 3,000 psi--.
Col. 5, line 36 reads "constant" but should read--content--.
Col. 5, line 44 reads "The examples demonstrate the process run with a buffer" but should read--This example demonstrates the process run without a buffer--.
Col. 5, line 45 reads "600 oxygen" but should read--600 psi oxygen--.
Col. 6, line 25 reads "preferably" but should read--preferable--.
Col. 6, line 34 reads "predominately" but should read--predominantly--.
Col. 7, line 14 reads "Nb" but should read--Nd--.
Col. 7, line 16 reads "temperature in the range of 150 - 150°C" but should read--temperature is in the range of 130 - 150°C--.
Col. 8, line 14 reads "$Nb_2O_3$" but should read--$Nd_2O_3$--.

Signed and Sealed this

Fifteenth Day of February 1977

[SEAL]

Attest:

RUTH C. MASON
Attesting Officer

C. MARSHALL DANN
Commissioner of Patents and Trademarks